(12) United States Patent
Makharinsky

(10) Patent No.: US 10,695,558 B2
(45) Date of Patent: Jun. 30, 2020

(54) SINGLE CONDUIT MULTI-ELECTRODE CARDIAC PACEMAKER AND METHODS OF USING THEREOF

(71) Applicant: Eagle Point Medical LLC, Dover, DE (US)

(72) Inventor: Leonid Makharinsky, Tal-Pieta (MT)

(73) Assignee: Eagle Point Medical LLC, Dover, DE (US)

( * ) Notice: Subject to any disclaimer, the term of this patent is extended or adjusted under 35 U.S.C. 154(b) by 204 days.

(21) Appl. No.: 16/035,653

(22) Filed: Jul. 15, 2018

(65) Prior Publication Data

US 2020/0016395 A1  Jan. 16, 2020

(51) Int. Cl.
| | | |
|---|---|---|
| *A61N 1/05* | (2006.01) | |
| *A61N 1/372* | (2006.01) | |
| *A61N 1/365* | (2006.01) | |
| *A61N 1/36* | (2006.01) | |

(52) U.S. Cl.
CPC ......... *A61N 1/056* (2013.01); *A61N 1/36592* (2013.01); *A61N 1/372* (2013.01); *A61N 1/36114* (2013.01)

(58) Field of Classification Search
CPC .... A61N 1/056; A61N 1/36592; A61N 1/372; A61N 1/36114; A61N 1/3686; A61N 1/0573; A61N 1/0565
See application file for complete search history.

(56) References Cited

U.S. PATENT DOCUMENTS

| | | |
|---|---|---|
| 5,083,564 A | 1/1992 | Scherlag |
| 5,251,643 A | 10/1993 | Osypka |
| 6,600,957 B2 | 7/2003 | Gadsby |
| 6,609,027 B2 | 8/2003 | Kroll |
| 6,684,109 B1 | 1/2004 | Osypka |
| 6,718,206 B2 | 4/2004 | Casavant |
| 6,898,465 B2 | 5/2005 | Gadsby |
| 6,907,299 B2 | 6/2005 | Han |
| 6,937,897 B2 | 8/2005 | Min |
| 7,027,876 B2 | 4/2006 | Casavant |
| 7,082,335 B2 | 6/2006 | Klein |
| 7,089,045 B2 | 8/2006 | Fuimaono |
| 7,228,164 B2 | 6/2007 | Fuimaono |
| 7,245,973 B2 | 7/2007 | Liu |
| 7,302,285 B2 | 11/2007 | Fuimaono |
| 7,326,204 B2 | 2/2008 | Paul |
| 7,326,205 B2 | 2/2008 | Paul |
| 7,326,206 B2 | 2/2008 | Paul |

(Continued)

OTHER PUBLICATIONS

Deshmukh P et al. Permanent, Direct His-Bundle Pacing a Novel Approach to Cardiac Pacing in Patients With Normal His-Purkinje Activation. Circulation. 2000;101:869-877.

(Continued)

*Primary Examiner* — Mark Bockelman
(74) *Attorney, Agent, or Firm* — Boris Leschinsky

(57) ABSTRACT

A device and method for providing cardiac pacing of triangle of Koch and bundle of His zones by multiple electrodes inserted using in a single conduit are provided. The method includes providing a single conduit with multiple electrodes, positioning electrodes in the target zone of a heart, selecting acceptable electrodes as active based on a predetermined criteria and providing cardiac stimulation for multiple chambers of the heart from a single location.

9 Claims, 13 Drawing Sheets

(56) References Cited

U.S. PATENT DOCUMENTS

| | | |
|---|---|---|
| 7,440,800 B2 | 10/2008 | Mower |
| 7,729,782 B2 | 6/2010 | Williams |
| 7,819,870 B2 | 10/2010 | Thao |
| 8,021,361 B2 | 9/2011 | Paul |
| 8,078,287 B2 | 12/2011 | Liu |
| 8,162,935 B2 | 4/2012 | Paul |
| 8,332,035 B2 | 12/2012 | Iaizzo |
| 8,391,995 B2 | 3/2013 | Efimov |
| 8,406,899 B2 | 3/2013 | Reddy |
| 8,428,715 B2 | 4/2013 | Ortega |
| 8,437,848 B2 | 5/2013 | Ortega |
| 8,447,399 B2 | 5/2013 | Mower |
| 8,460,286 B2 | 6/2013 | Stangenes |
| 8,538,521 B2 | 9/2013 | Zhu |
| 8,606,369 B2 | 12/2013 | Williams |
| 8,644,927 B2 | 2/2014 | Imran |
| 8,672,936 B2 | 3/2014 | Thao |
| 8,679,109 B2 | 3/2014 | Paul |
| 8,731,662 B2 | 5/2014 | Imran |
| 8,761,880 B2 | 6/2014 | Maskara |
| 8,825,155 B2 | 9/2014 | Zhu |
| 8,838,237 B1 | 9/2014 | Niazi |
| 8,942,805 B2 | 1/2015 | Shuros |
| 8,954,142 B2 | 2/2015 | Ek |
| 8,954,145 B2 | 2/2015 | Lee |
| 9,022,962 B2 | 5/2015 | Brown |
| 9,138,160 B2 | 9/2015 | Imran |
| 9,216,280 B1 | 12/2015 | Hakki |
| 9,289,593 B1 | 3/2016 | Hakki |
| 9,381,361 B2 | 7/2016 | Giovangrandi |
| 9,533,140 B2 | 1/2017 | Ek |
| 9,549,708 B2 | 1/2017 | Mercanzini |
| 9,764,142 B2 | 9/2017 | Imran |
| 10,406,370 B1 * | 9/2019 | Makharinsky ....... A61N 1/3624 |
| 2002/0082658 A1 | 6/2002 | Heinrich |
| 2002/0120318 A1 | 9/2002 | Kroll |
| 2003/0040676 A1 | 2/2003 | Prentice |
| 2003/0050637 A1 | 3/2003 | Maguire |
| 2003/0105492 A1 | 6/2003 | Ding |
| 2003/0212436 A1 | 11/2003 | Brown |
| 2004/0064176 A1 | 4/2004 | Min |
| 2005/0131464 A1 | 6/2005 | Heinrich |
| 2005/0267467 A1 | 12/2005 | Paul |
| 2008/0091192 A1 | 4/2008 | Paul |
| 2008/0140139 A1 | 6/2008 | Heinrich |
| 2009/0093859 A1 | 4/2009 | Ortega |
| 2010/0016917 A1 | 1/2010 | Efimov |
| 2010/0228308 A1 | 9/2010 | Cowan |
| 2010/0318147 A1 | 12/2010 | Forslund |
| 2011/0230922 A1 | 9/2011 | Fishel |
| 2012/0101539 A1 | 4/2012 | Zhu |
| 2013/0116740 A1 | 5/2013 | Bornzin |
| 2013/0123870 A1 | 5/2013 | Heinrich |
| 2013/0123872 A1 | 5/2013 | Bornzin |
| 2013/0158621 A1 | 6/2013 | Ding |
| 2014/0067036 A1 | 3/2014 | Shuros |
| 2014/0172035 A1 | 6/2014 | Shuros |
| 2014/0228713 A1 | 8/2014 | Thao |
| 2014/0249604 A1 | 9/2014 | Brown |
| 2014/0276929 A1 | 9/2014 | Foster |
| 2015/0094783 A1 | 4/2015 | Brown |
| 2015/0134022 A1 | 5/2015 | Lee |
| 2015/0151109 A1 | 6/2015 | Ek |
| 2016/0022998 A1 | 1/2016 | Imran |
| 2016/0136434 A1 | 5/2016 | Lee |
| 2016/0346532 A1 | 12/2016 | Shelton et al. |
| 2017/0080210 A1 | 3/2017 | Mercanzini |
| 2017/0087352 A1 | 3/2017 | Ek |
| 2017/0291022 A1 | 10/2017 | Shuros et al. |
| 2018/0214689 A1 | 8/2018 | Zhang |

OTHER PUBLICATIONS

Temple IP et al. Connexins and the atrioventricular node. Heart Rhythm 2013;10:297-304.

Mulpuru SK et al. Synchronous ventricular pacing with direct capture of the atrioventricular conduction system: Functional anatomy, terminology, and challenges. Heart Rhythm 2016;13:2237-2246.

* cited by examiner

SINGLE CONDUIT MULTI-ELECTRODE CARDIAC PACEMAKER AND METHODS OF USING THEREOF

BACKGROUND OF THE INVENTION

The present invention relates generally to cardiac pacing. More particularly, the invention describes multiple embodiments of a single-conduit multi-electrode cardiac pacemaker configured for stimulating the bundle of His and surrounding areas for pacing the entire heart and methods of using thereof.

In a healthy heart, a heartbeat originates in a specialized cardiac conduction system and spreads via this system to all parts of the myocardium. The structures that make up the conduction system are the sinoatrial node (SA node), the internodal atrial pathways, the atrioventricular node (AV node), the bundle of His and its branches, and the Purkinje system. Activation spreads quickly across the atria to the AV node, which then delays the wave of excitation. The delay enables the atria to contract before the ventricles contract. After the activation is delayed by, and leaves, the AV node, it enters and excites the bundle of His. This excitation of the bundle of His spreads in a precise pattern to the ventricles through the ventricular conduction system composed of Purkinje fibers. Excitation spreading through this system activates each ventricular cell at a precise time to produce a coordinated ventricular contraction. These events are seen generally as a normal QRS signal composed of group of waveforms on electrocardiogram (ECG) representing ventricular depolarization.

For various reasons, this process of normal propagation of the electrical excitation wave throughout the heart may be disrupted leading to a variety of conduction abnormalities and subsequently to abnormal heart contractility. Many such abnormalities may be seen on the ECG signal and can be detected as distorted or absent P-wave or QRS signal. Such abnormalities may be treated by using an implantable cardiac pacemaker configured to generate artificial pacing signals when natural excitation/conduction is disrupted or absent altogether.

Traditional pacemakers include typically 2 or 3 individual wires or leads that extend separately to different chambers of the heart and provide electrical stimulation from different locations within the heart. In modern pacemakers, each individual electrode may be activated in a unipolar mode using the body of the implanted pacemaker itself for example as a ground electrode. More recently, a bipolar mode of electrode activation is used in which each individual lead is equipped with a second ring electrode (usually serving in an anode capacity) which may be spaced apart from the negative (cathode) electrode. The ring electrode may or may not be in touch with the cardiac tissue but still supports the activation of the main electrode via conduction through blood in the vicinity thereof.

Recent experience with cardiac pacing indicates that traditional pacing sites may not be ideal for a good number of patients. Particularly, this is the case for right ventricular pacing, which may result in decline in heart function in some patients due to asynchronous cardiac contraction. Therefore, new direction in pacing is needed to avoid asynchronous cardiac contraction. This was attempted by pacing directly into the natural conduction system of the heart and more specifically—stimulating the bundle of His. This area is located right in the center of the heart in close proximity to atrial and ventricular tissue—and therefore may allow stimulation of one or multiple chambers of the heart from essentially the same location.

Permanent His bundle pacing (PHBP) has a potential to be used for treatment of at least some of the conduction abnormalities such as for example intra- and infra-hisian block including a complete heart block and left bundle branch block (Barba-Pichardo R, Moriña-Vázquez P, Venegas-Gamero J, Maroto-Monserrat F, Cid-Cumplido M, Herrera-Carranza M. [Permanent His-bundle pacing in patients with infra-Hisian atrioventricular block]. Rev Esp-Cardiol. 2006; 59(6):553-558; Lustgarten D L, Calame S, Crespo E M, Calame J, Lobel R, Spector P S. Electrical resynchronization induced by direct His-bundle pacing. Heart Rhythm. 2010; 7(1):15-21; Kronborg M B, Mortensen P T, Gerdes J C, Jensen H K, Nielsen J C. His and para-His pacing in AV block: feasibility and electrocardiographic findings. J Interv Card Electrophysiol. 2011; 31(3):255-262; Sharma P S, Vijayaraman P. His Bundle Pacing Or Biventricular Pacing For Cardiac Resynchronization Therapy In Heart Failure: Discovering New Methods For An Old Problem. J Atr Fibrillation. 2016; 9(4):1501; Herweg B, Gerczuk P Z, Sofi A, Vijayaraman P, Barold S S. Permanent His Bundle Pacing in Intra-Hisian Conduction Block: Mechanistic Insights. J Electrocardiol. 2017; 50(6):933-936.).

In patients undergoing pacemaker implantation, PHBP was found to be associated with reduction in death or heart failure hospitalization during long-term follow-up compared to a more conventional right ventricular pacing. Bundle of His pacing was also associated with higher rates of lead revisions and generator change. (Vijayaraman P, Naperkowski A, Subzposh F A, et al. Permanent His-bundle pacing: Long-term lead performance and clinical outcomes. Heart Rhythm. 2018:15(5); 696-702). In patients with heart failure and left bundle branch block, PHBP, as an alternative means to achieve cardiac resynchronization, has been shown to be feasible (Lustgarten D L, Crespo E M, Arkhipova-Jenkins I, et al. His-bundle pacing versus biventricular pacing in cardiac resynchronization therapy patients: A crossover design comparison. Heart Rhythm. 2015; 12(7): 1548-1557) and possibly beneficial compared to biventricular pacing (Sharma P S, Dandamudi G, Herweg B, et al. Permanent His-bundle pacing as an alternative to biventricular pacing for cardiac resynchronization therapy: A multicenter experience. Heart Rhythm. 2018; 15(3):413-420).

Despite the recent technological progress with the design of electrophysiology (EP) mapping catheters and pacing leads, their ability to reliably reach the target area at and surrounding the bundle of His in patients with broad anatomical variations is very limited.

Currently, successful placement of the pacing lead to a bundle of His is only achieved in approximately 80% of the cases (Vijayaraman P, Dandamudi G, Zanon F, et al. Permanent His bundle pacing: Recommendations from a Multicenter His Bundle Pacing Collaborative Working Group for standardization of definitions, implant measurements, and follow-up. Heart Rhythm. 2018; 15(3):460-468). This is frequently due to the inability to attach the electrode to a successfully identified target site with a reasonable capture threshold. To this day, the area to deploy the pacing electrode is identified by traditional methods of a multipolar electrode catheter used as a rough guide in a point-by-point electrogram mapping. Additionally, determination of the bundle of His capture is not always clear or easy to determine clinically.

Conventionally, a single electrode is used for probing and searching for the best position for implantation. Such probing procedure uses a temporary attachment of the electrode to the endocardial surface of the cardiac tissue followed by successive cardiac stimulation starting at higher voltages and subsequently reducing the voltage until the response of the cardiac tissue is no longer observed on the ECG—so as to determine a threshold for the lowest effective stimulation voltage. If the desired ECG response cannot be achieved at all or can be achieved only at high voltages, the electrode is disconnected from the tissue and moved to another location where the process is repeated again. As more than one cardiac chamber stimulation is frequently desired, this process may be time consuming and may involve large number of fluoroscopy images—leading to increased radiation exposure for both the patient and the physician.

The lead placement therefore is dependent on a point-by-point mapping and pacing using a trial-and-error methodology. The need therefore exists for better pacing tools and pacing leads to achieve a more rapid and effective permanent cardiac pacing. The need also exists to resolve a guidance problem of the pacing leads and achieve a reproducible navigation to predetermined capture sites—so as to improve the operator's confidence, expedite the process of lead implantation and reduce radiation exposure due to excessive fluoroscopy imaging.

BRIEF SUMMARY OF THE INVENTION

Accordingly, it is an object of the present invention to overcome these and other drawbacks of the prior art by providing a novel single conduit cardiac pacemaker configured for electrical evaluation and stimulation of the bundle of His and surrounding areas including the atrium.

It is another object of the present invention to provide a single conduit cardiac pacemaker configured for reliable and deterministic implantation in a broad range of patients with a variety of anatomical variations and abnormalities in electrical conduction of the cardiac tissue.

A further object of the present invention is to provide a single conduit cardiac pacemaker and methods of using thereof allowing to rapidly identify best stimulation sites after implantation and to provide cardiac pacing without a need to implant multiple individual electrodes.

In embodiments, the novel single conduit multi-electrode pacemaker comprises a single elongated insulated conduit housing a plurality of electrical conductors operably connected to a plurality of respective individual electrodes at the distal end of the conduit. Individual electrodes may be configured to be retained near the center of the conduit while constrained by a surrounding sheath. Retraction of the sheath allows the electrode to spread out radially away from the center so as to allow simultaneous implantation into the target area of the cardiac tissue. As a result, a plurality of spaced apart electrodes may be positioned in the cardiac tissue via a single implantation procedure. A central tissue attachment spring may also be provided to secure the conduit and all the individual electrodes in place. Individual position of the electrodes may be selected to reliably cover the target area of the cardiac tissue such as the bundle of His with at least some of the electrodes located in and around this selected target area which may include the atrial tissue.

In other embodiments, following the positioning of the plurality of electrodes in and around the target area of the cardiac tissue, individual interrogation of these electrodes may be conducted with the aim of identifying desired electrodes located directly at the target site. Those electrodes that do not provide desired ECG response during test stimulation may be abandoned. If more than one electrode is found to provide desired stimulation behavior, additional selection within this group may be conducted to identify one or more electrodes with the lowest threshold for effective cardiac stimulation.

In further embodiments, a method of providing cardiac pacing includes the steps of providing a flexible single conduit housing a plurality of individual wires extending therethrough and terminating with a plurality of corresponding individual electrodes located at the distal end of the conduit; advancing the single conduit to position a distal end thereof near a cardiac tissue target area while the plurality of individual electrodes are held in a collapsed position next to a center of the distal end of the single conduit; expanding the plurality of individual electrodes to an expanded position forming a predetermined expanded pattern of the individual electrodes about and away from the center of the distal end of the single conduit; advancing the single conduit to implant the individual electrodes into the cardiac tissue target area; interrogating the plurality of individual electrodes to determine a subset of the individual electrodes meeting a predetermined acceptance criteria; and initiating cardiac pacing using at least some of individual electrodes of the subset of individual electrodes meeting the predetermined acceptance criteria, these at least some individual electrode connected to a pacemaker.

Permanent pacing may then be initiated with an implantable pacemaker using a subset of the plurality of electrodes that are best matched to desired cardiac pacing outcome.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
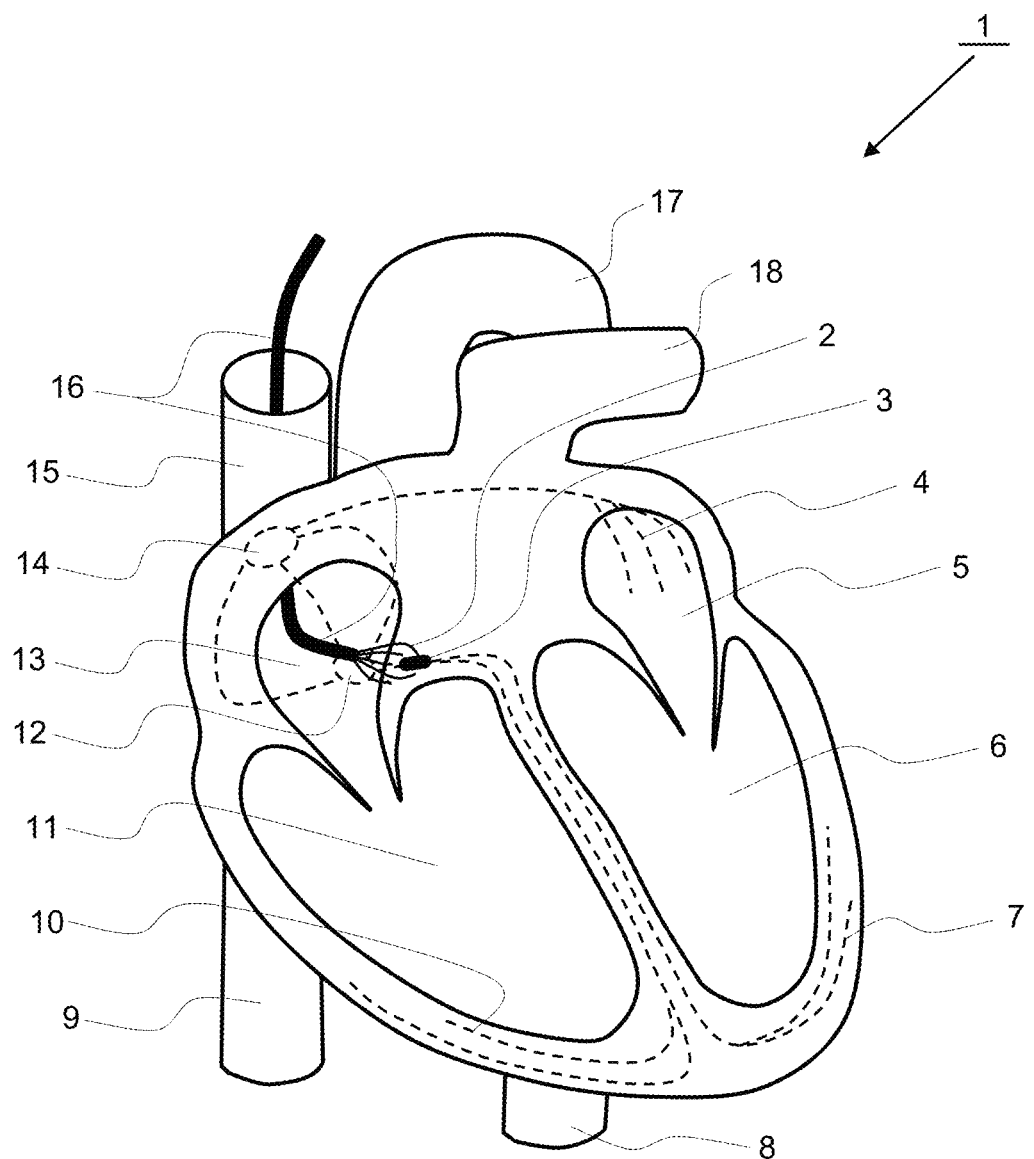
FIG. 1 is a general cross-sectional view of a heart with implanted multiple electrodes into a target zone.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The present invention describes a single cardiac pacing conduit with a plurality of individual electrodes located at the distal end thereof. Initially, individual electrodes are located in a compressed state next to the center of the conduit—so as to facilitate easy insertion and advancement to the implantation site. While in the vicinity of the desired implantation site, individual electrodes are expanded away from the center so as to form a plurality of electrodes configured to cover the target area of the cardiac tissue. The conduit is then advanced further and all electrodes are implanted into the cardiac tissue at the desired site. Location of individual electrodes may be selected to provide adequate coverage of the target area and surrounding tissues so that at least a subset of electrodes may be useful for subsequent cardiac pacing.

Once implantation of individual electrodes is accomplished (with optional temporary or permanent tissue attachment to secure the electrodes in place), individual or group interrogation of the electrodes may commence. To evaluate individual electrodes, one electrode at a time may be activated in a unipolar or bi-polar mode with various levels of pacing voltage so as to determine whether its location and performance is adequate for desired cardiac pacing purposes. Evaluation of all electrodes may be conducted using one electrode at a time or pairing electrodes with each other. As a result, preferred subset of electrodes may be identified so as to determine the best individual electrodes or pairs of electrodes suitable for subsequent pacing purposes with the lowest effective voltage thresholds.

In embodiments, covering the bundle of His and triangle of Koch as well as surrounding areas of cardiac tissues may result if identifying electrodes suitable for atrial pacing, selective bundle of His pacing or mixed pacing. Depending on the nature of cardiac abnormalities, a final selection of electrodes may be conducted aimed at identifying the best electrodes located at the proper target area for each individual patient.

In situations when no electrodes are found to be suitable for subsequent cardiac pacing, repositioning and re-implantation of the plurality of electrodes may be conducted so as to attempt to relocate the plurality of electrodes in another position so as to allow another attempt to find one or more electrodes suitable for permanent cardiac pacing. Remaining electrodes may be abandoned and not used for cardiac pacing following such interrogation procedure. These remaining electrodes may remain passive but can be optionally re-activated in the future if the cardiac disease progresses and a different mode of pacing is needed for the patient later in life. Another reason to leave passive electrodes in place is to allow optional activation thereof in case of lead fracture or another malfunction of the initially selected electrodes. Having other electrodes suitable for cardiac pacing may prevent immediate complications when switching to their use is done automatically by a suitable cardiac pacemaker operably connected to and programmed to perform such switch in this case. A further yet advantage of providing additional electrodes is to avoid a surgical intervention to replace the entire conduit when one of the electrodes experienced a malfunction.

Specific embodiments of the present invention are now described in greater detail.

Referring to FIG. 1, a human heart 1 is illustrated in a general way with implanted therein a conduit of the invention 16 having multiple electrodes 2 extending from a distal end thereof and into a target zone in the heart. Seen in the drawing are the following elements and heart structures: distal electrodes 2 are extending from the distal tip of the conduit 16 into the target zone, which includes bundle of His 3. Bachmann's bundle 4 is seen as a conduction structure. Also shown are the left atrium 5, left ventricle 6, left conduction bundle (or left bundle branch) 7, descending aorta 8, inferior vena cava 9, right conduction bundle (or right bundle branch) 10, right ventricle 11, atrioventricular node 12, right atrium 13, sinoatrial node 14, and a superior vena cava 15. As with other pacing leads, a pacing conduit 16 of the invention may be minimally invasively delivered through the superior vena cava 15, aorta 17, or left pulmonary artery 18.

Figure 2:
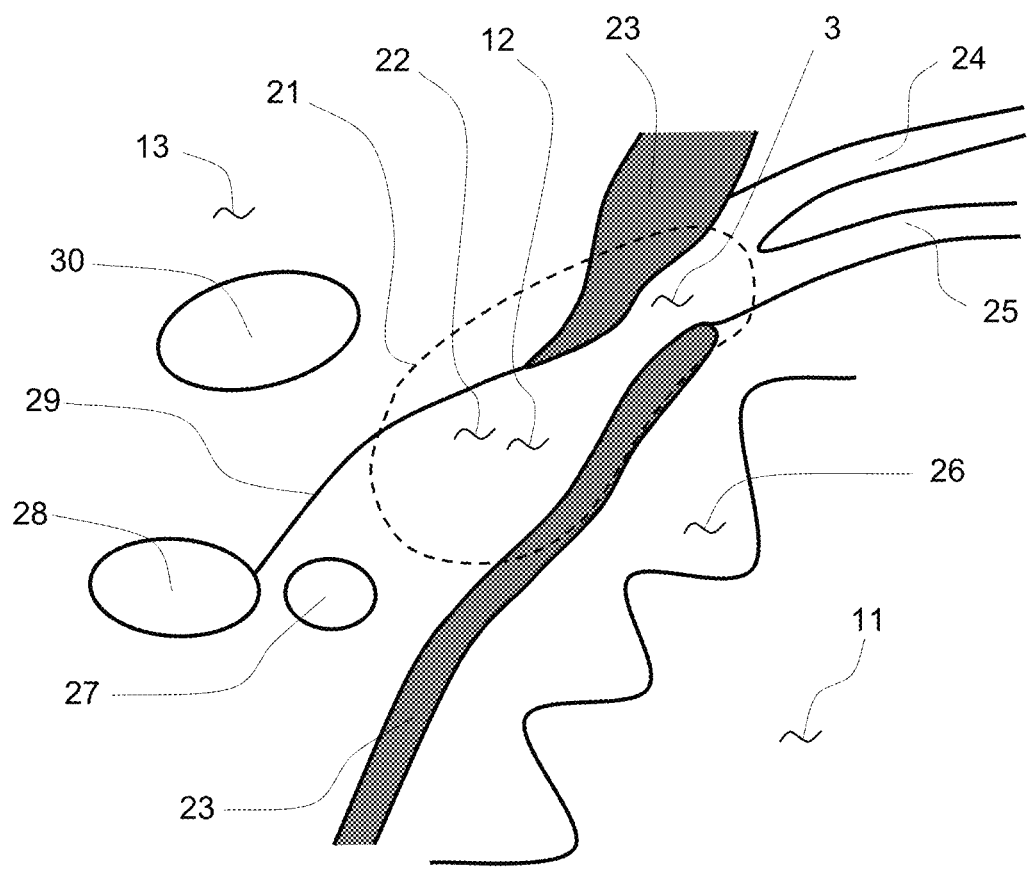
FIG. 2 is a schematic view of a close-up portion of the heart of FIG. 1 including the triangle of Koch and bundle of His as the target zone.

FIG. 2 shows a schematic view of a portion of the heart of FIG. 1 including the triangle of Koch 22 and bundle of His 3 that together and along with surrounding atrial tissues may be contemplated as the target area 21 suitable for implantation of a plurality of pacing electrodes 2. The target area 21 may be accessed through the right atrium 13. To allow distinct pictorial identification of the proper location of the target area 21, the following heart anatomical and functional structures are depicted in FIG. 2: left bundle branch 24, right bundle branch 25, tricuspid valve 26, coronary sinus ostium 27, inferior vena cava 28, tendon of Todaro 29, and fossa ovalis 30. The penetrating bundle of His 3 is a structure consisting of specialized conducting tissue located within the membranous portion of the ventricular septum. Bundle of His is surrounded by connective tissue from the central fibrous body 23, which constitutes an insulating layer to the chord-like bundle. Referring to FIGS. 1 and 2, the compact atrioventricular node 12 located in the right atrium 13 within the triangle of Koch 22 serves as the gateway of electrical conduction to the ventricles 6 and 11. Anatomic target area 21 may be intended for stimulatory pacing electrodes making contact with (a) the penetrating Bundle of His and surrounding areas, which traverses through the membrane of septum, and (b) conduction elements of the triangle of Koch 22 and surrounding areas. This target area for electrodes implantation may be selected to allow controlled pacing of one or multiple myocardial structures.

At least some of the individual electrodes may be targeted for implantation into the atrial tissues located in the vicinity of the target area 21. Activation of these electrodes may be used for conventional atrial pacing. The approach of implanting some electrodes into the bundle of His while some other electrodes into the atrial tissues nearby may be advantageous for allowing cardiac pacing of both the atrium (using atrial electrodes) and the one or both ventricles of the heart (using electrodes in the bundle of His)—all from the same single implantation procedure and using the same conduit for activation thereof.

Figure 3A:
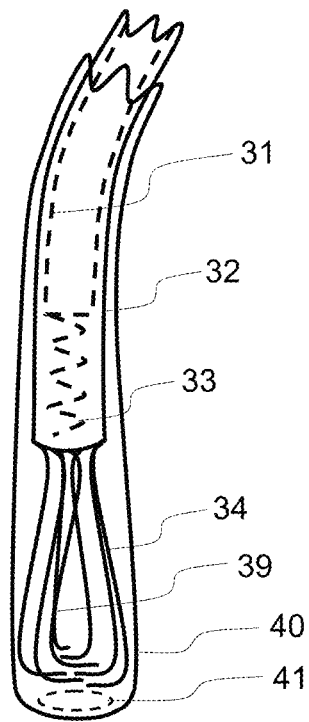
FIGS. 3A, 3B, and 3C are perspective views of a tip of a conduit with multiple electrodes according to the first embodiment of the invention.
Figure 3B:
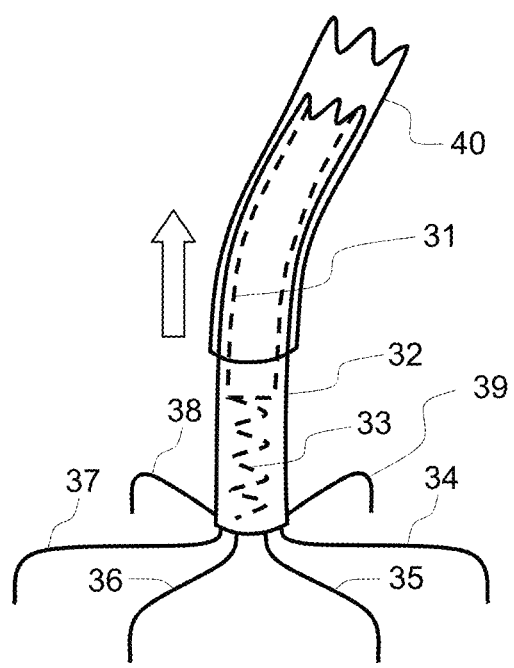
Figure 3C:
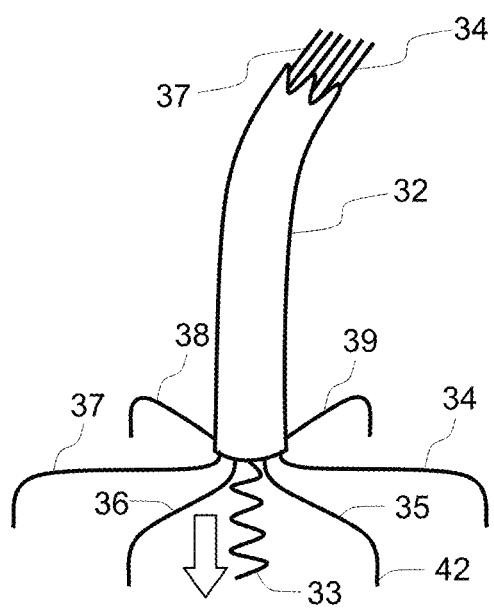

FIGS. 3A, 3B, and 3C show perspective views of a distal tip of the conduit of the invention with multiple electrodes according to the first embodiment thereof. Specifically, FIG. 3A shows the compressed assembly of individual electrodes illustrated during the steps of delivery to the heart target area. The electrode assembly may include a tissue attachment spring/screw portion 31 designed to deliver spring/screw 33 initially hidden inside the distal end of the conduit 32, as well as a plurality of pacing electrodes 34-39 located distally of the screw 33. Individual electrodes 34-39 may be made into a Z-shape and initially compressed and placed within the insulating outer sheath 40 with opening 41 distally. The tissue attachment screw 33 may also be configured to serve itself as an electrode. The number of individual electrodes can be 2, 3, 4, 5, 6, 7, 8, 9, 10, 11, 12, 13, 14, 15, or 16 electrodes. Each individual electrode or a group of individual electrodes may be equipped with an individual wire connecting the respective electrode or a group of electrodes to the pacing device on the other end of the single conduit 31. In embodiments, effective and efficient delivery of electrical energy to the myocardium via the individual electrodes 34-39 can be achieved by incorporation of steroid-elution into the individual electrode tips 42 (electrode-tissue interface) that allows reliable heart pacing with low stimulation threshold.

Spaced proximally from the individual electrodes along the conduit 32 there may be provided a ring electrode (not shown), which may be used for bipolar pacing purposes or individual electrode interrogation purposes.

After placing the conduit 32 in the vicinity of the target area, the sheath 40 may be retracted backwards to reveal the distal end of the conduit 32, as shown by an arrow in FIG. 3B directed up. This allows individual electrodes 34-39 to be released to spring outwards and away from the central axis of the lead 32 and spread radially around the lead 32. At this stage, rotating the distal end of the lead 32 allows changing the position of electrode tips if desired. Once the desired orientation and position of individual electrodes is achieved, the distal end of the lead 32 may be advanced forward to allow the tips 42 of individual electrodes to penetrate into the cardiac tissue as seen in FIG. 3C. The screw 33 may be advanced forward from the inside cavity of the conduit 32 and rotated to secure the entire assembly of individual electrodes to the cardiac tissue as shown by an arrow directed down.

Those skilled in the art will recognize that screw 33 can be shorter than 5 mm and longer than 3 mm. Also, those skilled in the art will recognize that individual electrodes 34-39 can cover the suitable target area with a diameter from about 5 mm to about 30 mm. In embodiments, the diameter of the circle formed by individual electrodes may be 5 mm, 10 mm, 15 mm, 20 mm, 25 mm, 30 mm or any size in between.

Following evaluation of electrical functionality of individual electrodes (described below in greater detail), the screw 33 may be retracted and the conduit 32 may be repositioned if needed until the proper function of at least some of the individual electrodes is achieved.

In embodiments, expanding individual electrodes released by retracting of the sheath 40 may form other geometrical figures in addition to a circle, for example they may form a line of dots representing individual electrodes, a spiral of dots, and other arrangements as the invention is not limited in this regard.

The material and design of the individual electrodes may follow a convention established for these devices. A biocompatible wire with suitable mechanical properties and electrical conductivity may be used to form an individual electrode capable of being stored in a compressed state inside the sheath 40 and when released spring outwards to a desired position for subsequent implantation into the cardiac tissue.

In yet further embodiments, some or all individual electrodes may be stacked along the conduit 32 along some length thereof so as to avoid crowding of all electrodes together and occupying the entire available cross-sectional area. In this case, the ends of electrodes 41 may be made longer for those electrodes which are moved away from the distal end of the conduit 32 so as to assure a uniform height of all individual electrodes upon release thereof from the sheath 40.

While in some embodiments, all individual electrodes 34-39 may be fixedly assembled within the conduit 32, in other embodiments individual electrodes may be organized together and placed within a lumen inside the conduit 32 so as to allow one or several individual electrodes to be removed after initial interrogation is complete.

Figure 4A:
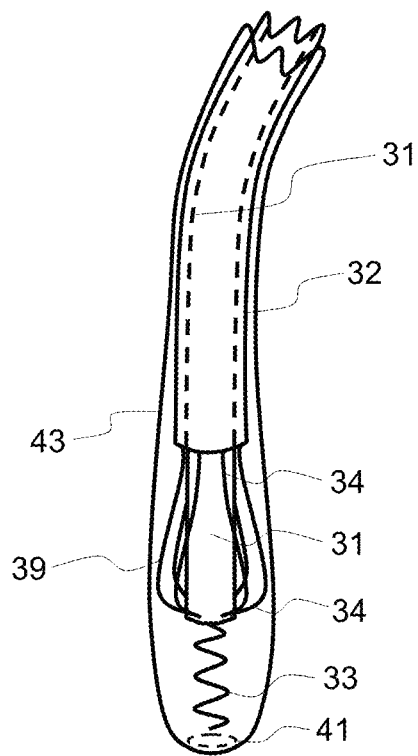
FIGS. 4A, 4B, and 4C are perspective views of a tip of a conduit with multiple electrodes according to the second embodiment of the invention.
Figure 4B:
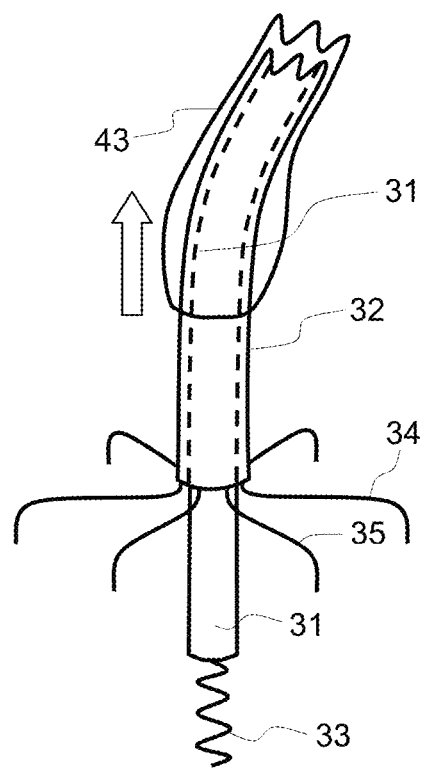

FIG. 4 presents a perspective view of a distal end of a single conduit with multiple electrodes according to the second embodiment of the present invention. Specifically, FIG. 4A shows the conduit assembly in a compressed state during delivery to the heart target area. The assembly includes a spring/screw tissue attachment portion 31 inside the conduit 32, spring/screw 33 in this case located distal to a plurality of multiple pacing electrodes 34-39, and outer insulating sheath 43 with opening 41 distally. The number of individual pacing electrodes can be 2, 3, 4, 5, 6, 7, 8, 9, 10, 11, 12, 13, 14, 15, or 16 electrodes. After retraction of the sheath 43, the conduit 32 is revealed, as shown by an arrow in FIG. 4B directed up, which in turn allows the electrodes 34-39 to spread radially and away from the distal tip of the conduit 32.

Figure 4C:
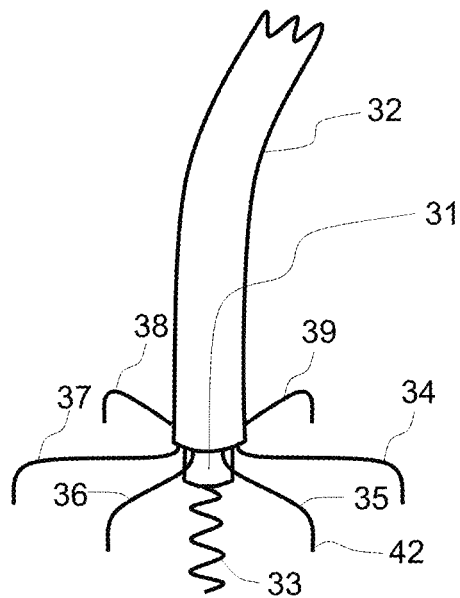

FIG. 4C shows the step when the conduit 32 is moved closer to the spring 33. After that, the spring 33, working optionally as an additional electrode or as a ground reference electrode, may be screwed into the tissue of target area and electrodes 34-39 may be advanced to penetrate the tissue of the target area as well. After the screw 33 enters the cardiac tissue, further manipulation (push forward and rotation) with the distal portion of the electrode wires may be used to reposition electrode tips to a more desired location.

Figure 5A:
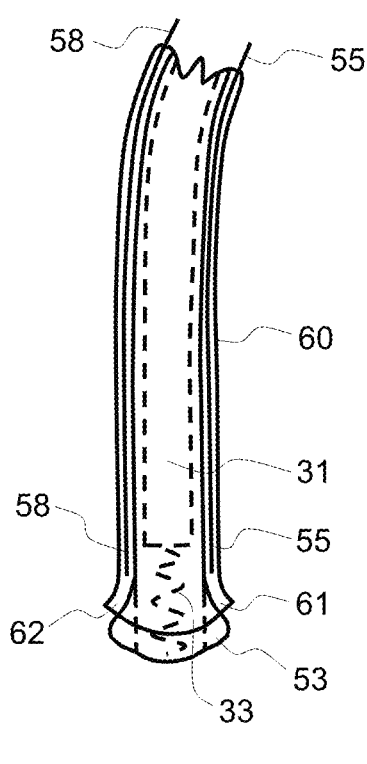
FIGS. 5A and 5B are perspective views of a tip of a conduit with multiple electrodes according to the third embodiment of the invention.

FIG. 5 presents a perspective view of a tip of a conduit with multiple electrodes according to the third embodiment of the present invention. More particularly, FIG. 5A shows the conduit assembly during the delivery to the heart target area. The assembly includes a spring/screw tissue attachment portion 31 which may be retracted and retained inside the distal portion of the conduit 60, spring/screw 33 extending from the portion 31, multiple pacing electrodes 55-58, and the outer insulating retractable sheath 43. The electrodes 55-58 may be arranged along the periphery of the conduit 60; every electrode may be placed in an individual delivery slot, e.g. electrode 55 may be located inside the slot 61, electrode 58 may be positioned inside the slot 62 and so on. Each slot may contain an exit shaped to direct each respective electrode on a trajectory diagonally outwards and away from the center of the conduit, for example using an enlargement 53 configured to deflect the electrodes as they are moved along their respective slots. In embodiments, the angle of direction for advancing each electrode diagonally outwards and away from the center may be from about 25 degrees to about 70 degrees to the central axis of the single conduit.

Figure 5B:
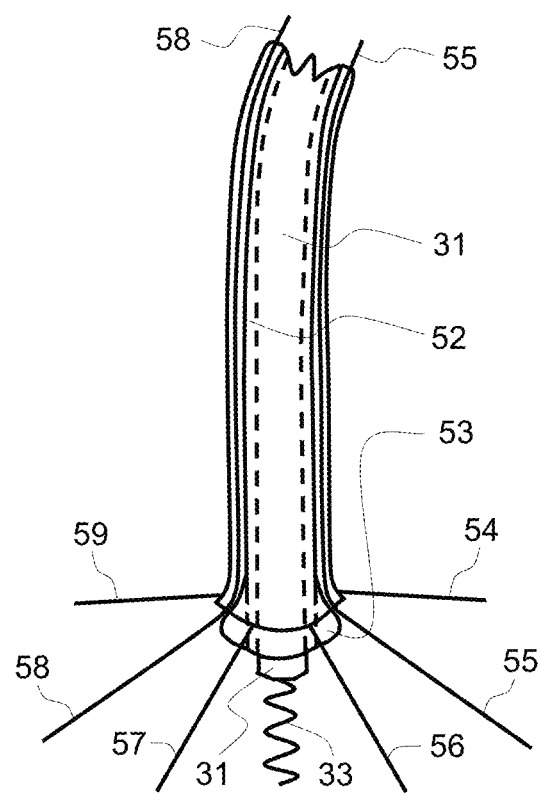

After the distal end of the conduit 60 is delivered to the target area, the screw tissue attachment portion 31 may be advanced out of the conduit 60 and exposed to the cardiac tissue as shown by an arrow in FIG. 5B. Further, the screw/spring 33 may be screwed into the cardiac tissue of target area. After that, individual electrodes 54-59 may be one by one or as a group (using a slider engaging some or all individual electrodes—not shown) advanced forward and inserted into the cardiac tissue of the target area.

One advantage of individual deployment of each electrode is that it may be positioned at various desired depths so as to adapt the generally circular pattern of electrodes to fit a particular geometry of the cardiac tissue for an individual patient. Another advantage of this design is that those individual electrodes that may not be selected for final inclusion in the cardiac pacing of the patient may be withdrawn from the single conduit so as not to be present to remain in the cardiac tissue in a passive role.

Figure 6A:
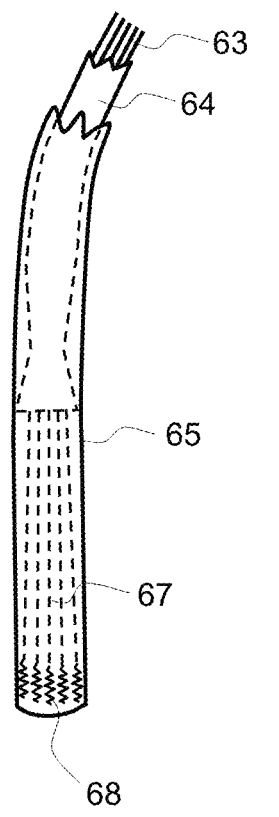
FIGS. 6A and 6B are perspective views of a tip of a conduit with multiple electrodes according to the fourth embodiment of the invention.

FIG. 6 presents a perspective view of a tip of a conduit with multiple electrodes according to the fourth embodiment of the present invention. Specifically, FIG. 6A shows the conduit assembly as compressed and configured for the delivery to the heart target area. The assembly may include a conduit 65, a movable portion 64 and multiple pacing electrodes 67. At least some or all individual electrodes may contain a tissue attachment spring/screw 68 at a distal tip thereof.

Figure 6B:
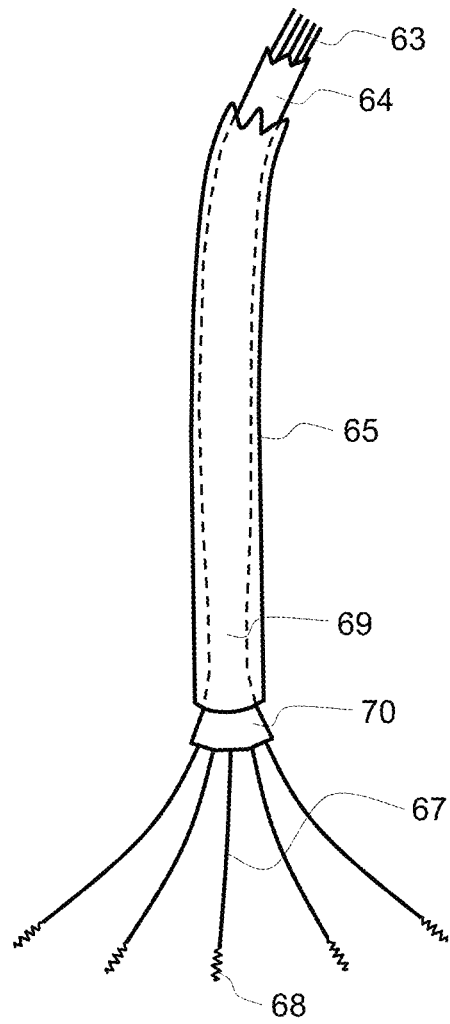

After delivery the lead tip to the target area for electrode implantation, the movable portion 64 may be retracted away from the conduit 65 as shown in FIG. 6B. The electrodes 67 may be configured to spring outwards and away from the center of the conduit, for example with the aid of a narrow neck 69 and enlarged conduit extension 70. Furthermore, one, several or every electrode 67 may be delivered individually and secured to the cardiac tissue of the target area by moving it up/down and rotating thereof using individual electrode wires 63 at the proximal end of the conduit of the invention.

Figure 7:
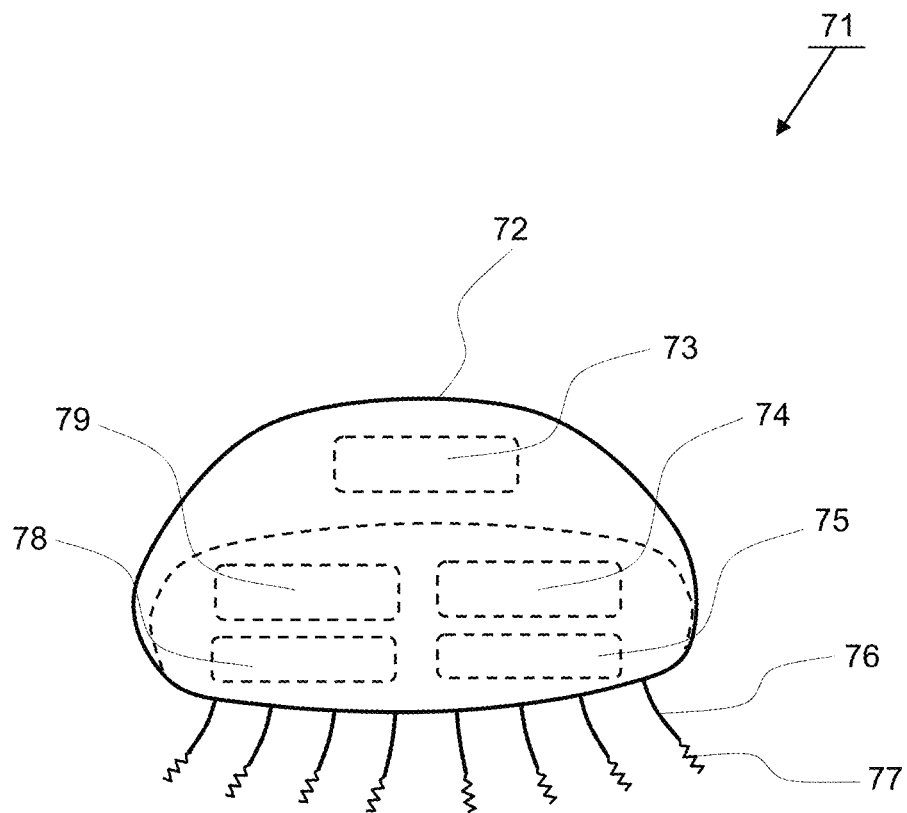
FIG. 7 is a view of an implantable pacemaker assembly with multiple electrodes according to the fifth embodiment of the present invention.

FIG. 7 shows a schematic diagram of a leadless implantable pacemaker 71 providing multiple electrodes. The pacemaker body 72 may be designed to cover multiple individual pacing electrodes 76 with tissue attachment springs at their respective ends/tips, wireless communicating microchip 73, programmable processing microchip 74, single source of electric power (battery) for energizing multiple electrodes 75 of the leadless pacemaker 71, electrode multiplexer 78 and a signal amplifier 79. One, some or every electrode may contain a spring/screw 77 at its tip for tissue attachment. After the delivery the pacemaker to the target area, the electrodes may be activated and advanced to penetrate the tissue of the target area. In embodiments the number of electrodes may be 2, 3, 4, 5, 6, 7, 8, 9, 10, 11, 12, 13, 14, 15, 16, 17, 18, 19, 20, 21, 22, 23 or 24 electrodes. In further embodiments, the leadless pacemaker 71 may have individual electrodes arranged as individually-activated zones on a surface thereof, avoiding some or all of spring/screw altogether. Tissue attachment may be provided by the external shape of the pacemaker 71 selected to provide adequate contact with the target cardiac tissue once implanted.

After implantation of the leadless pacemaker 71 to a target area of cardiac tissue as described elsewhere in the specification, multiple individual electrodes 75 may be interrogated to determine a subset thereof meeting a predetermined acceptance criteria, after which these selected active electrodes may be operated to provide electrical stimulation of multiple chambers of the heart from a single location, using a single pacemaker with a single battery to operate multiple active electrodes 75.

Figure 8:
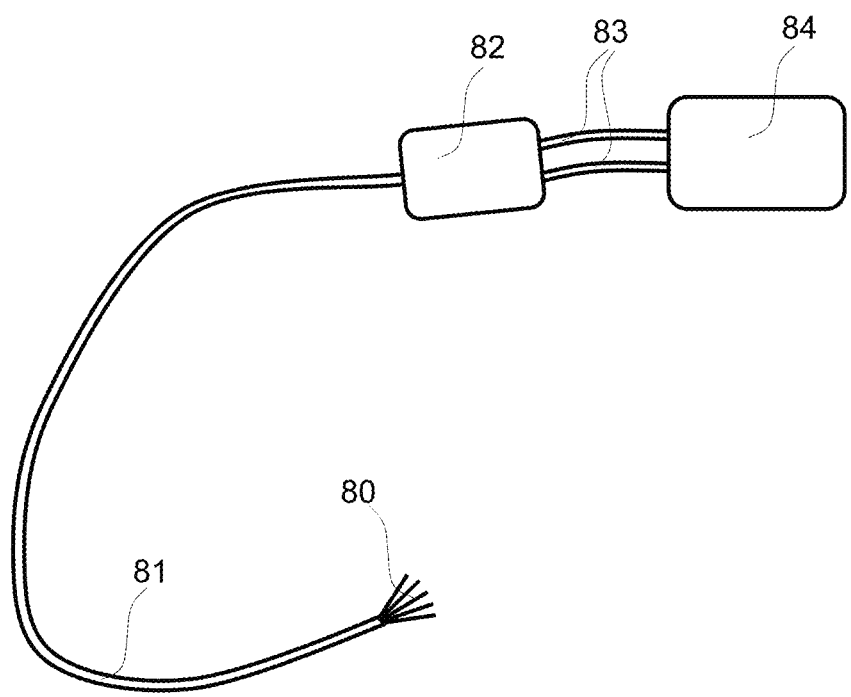
FIG. 8 is a schematic diagram of a cardiac pacemaker with a single conduit combining multiple electrodes therein.

In addition to providing a dedicated pacemaker to activate all electrodes of the above described embodiments of the conduit of the invention, it is contemplated that a multiplexer can be used to allow using a conventional pacemaker with the conduit of the invention. FIG. 8 shows a schematic diagram of a pacemaker of the present invention having a single lead with multiple electrodes at the distal end thereof. The pacemaker may comprise multiple electrodes 80 configured for implantation into cardiac tissue of the target area, a single conduit 81 for individual electrical connections with multiple electrodes 80, and a multiplexer 82 for communicating the multiple electrode connections to the standard electrical inlet/outlet connections 83 of currently available pacemakers. The multiplexer may be configured to allow connecting suitable electrodes to the pacemaker connections 83 at an appropriate time during the cardiac cycle. In one example, connectors 83 may be connected by the multiplexer 82 to the individual electrodes 80 selected for atrial pacing during the first part of the cardiac cycle. This may be used to provide a suitable P-wave stimulation to the atria of the heart. At a later portion of the cardiac cycle, the multiplexer 82 may be configured to connect other individual electrodes 80 to the connections 83, this time activating those individual electrodes 80 that are selected during the implantation procedure for stimulating the His bundle and cardiac ventricles with an electrical impulse generating a QRS complex.

In use, the single conduit of the present invention may be advanced through the blood vessels or subcutaneously towards the heart as in a conventional pacemaker implantation procedure. Once the distal end of the conduit is located in the vicinity of the target area, the outer sheath may be retracted over the conduit (or another deployment mechanism may be activated) so as to reveal multiple individual electrodes. The electrodes may be then urged to spread away from the center of the distal end of the conduit to assume a predetermined expanded pattern.

After final positioning of the plurality of electrodes in the expanded pattern over the target cardiac tissue area, the conduit may be further advanced forward and individual electrodes may be caused to be implanted into the cardiac tissue. Using the conduit of the present invention, all individual electrodes may be implanted at the same time or closely following each other—a key advantage in time savings and reduction in radiation exposure to the patient and the physician.

Individual electrodes at the proximal end of the conduit may then be connected to a pacemaker programming device—individually, in groups, or via a multiplexer. Following this implantation and electrical connection procedure, individual interrogation of each electrode or groups of electrodes may be commenced.

In embodiments, individual electrodes may be evaluated one by one or in groups following a similar approach used for evaluating single electrodes in a traditional pacemaker implantation procedure. In one example, each individual electrode may be fully characterized by applying cardiac pacing impulses at various voltages (typically in a descending pattern) in a unipolar or bipolar mode so as to determine a response from the heart. The heart response may be determined using for example an ECG signal collected internally close to the heart and/or externally using skin electrodes.

If positioned properly, an expanded pattern of electrodes may cover the target area including the triangle of Koch and the bundle of His as well as surrounding atrial tissues. Collecting response signals from interrogation of each individual electrodes may produce three families of responses—that of (i) pure atrial pacing, (ii) mixed signal pacing, and (iii) pure ventricular pacing resulting from stimulation of the bundle of His. Based on collected results, all individual electrodes may be separated into those producing one of these three signal patterns and others that may or may not be useful for pacing purposes. Within these groups of individual electrodes divided into groups based on their respective recorded responses, further separation may be attempted, for example individual electrodes may be ranked based on the level of minimally effective threshold—lower threshold electrodes may be preferred for activation on a continuous basis so as to conserve the electrical energy of the pacemaker and to extend the useful life of the pacemaker battery.

Acceptance for cardiac atrium pacing may be determined using a first predetermined acceptance criteria, for example appearance of an acceptable P-wave on the ECG tracing at the lowest stimulating voltage. Similarly, acceptance for cardiac ventricle pacing may be determined using a second predetermined acceptance criteria, for example appearance of an acceptable QRS signal on the ECG tracing at the lowest stimulating voltage.

In embodiments, alternative acceptance criteria may be a confirmed selective or non-selective capture of the bundle of His as may be preferred for pacing needs of a particular patient.

Depending on the nature of cardiac arrhythmia for a particular patient defining a specific pacing need therefor, a final selection of the most useful electrodes may be conducted so as to assure a reliable stimulation arrangement for a particular patient.

As an alternative to a unipolar interrogation of each individual electrode, a bipolar interrogation using an optional ring electrode or a central screw electrode may be conducted if that offers any advantage for a particular patient.

In further embodiments, individual electrodes may be paired so as to conduct interrogation of certain pairs of electrodes. In this case, if the total number of electrodes is not excessively high, all combinations of pairs of electrodes may be evaluated. If however, there is a high number of electrodes present and conducting evaluation of each possible combination of electrodes is time consuming, additional selection methods may be deployed. In one example, a subset of acceptable individual electrodes may be stratified further by each electrode first undergoing a determination of the lowest voltage threshold for its stimulating efficacy, followed by selecting of the top few electrodes that exhibit the best stimulating pattern at the lowest voltage. Following such initial selection, these top selected electrodes may be evaluated in pairs to determine their best combination suitable for stimulating purposes for a particular patient.

In case none or only a few electrodes are exhibiting satisfactory performance, the conduit may be disconnected from the cardiac tissue and moved to another location so as to implant the plurality of individual electrodes at a better site in cardiac tissue. Following a repositioning of the electrodes, another round of testing as described above may be commenced to proceed until a suitable number and combination of individual electrodes may be found to satisfy pacing needs for a patient.

In further embodiments, as opposed to fully evaluating each individual electrode by supplying a series of characterizing stimulating impulses thereto and then moving to the next individual electrode, all electrodes may be evaluated with the same initial characterizing impulse supplied to individual electrodes one at a time. Following detection of response from each individual electrode to the same initial impulse, a second impulse can be used to interrogate all electrodes followed by the third impulse, fourth impulse etc. One advantage of this technique is that the first impulse may be selected to be at a low voltage, the second impulse may be at a higher voltage, and subsequent impulses may be of yet higher predetermined voltage levels. This approach may be advantageous when increasing the voltage of the circulating impulse so as to determine when at least one or a subset of the individual electrodes start to exhibit desired stimulating efficacy and a suitable response from the heart. Once that is achieved, further interrogation may be stopped—so as to conduct evaluation of all available electrodes in a shorter period of time.

Figure 9:
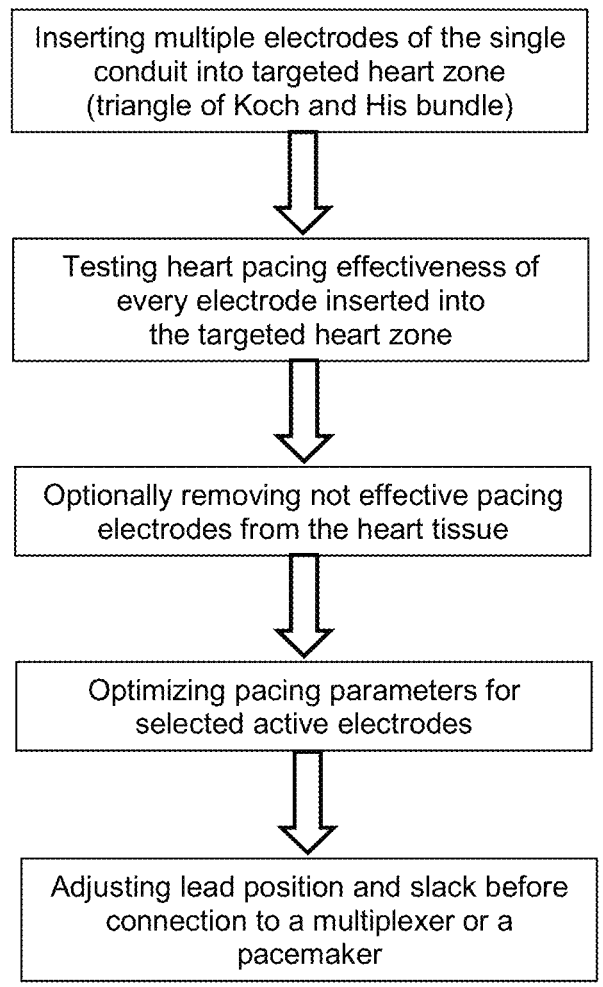
FIG. 9 is a block diagram illustrating the sequence of the steps according to one method of the invention.

FIG. 9 shows a block diagram illustrating an exemplary sequence of steps of the method of using the cardiac pacemaker of the invention. The method may include the steps of inserting multiple pacing electrodes of the single conduit into target heart zone (triangle of Koch and bundle of His), individually testing heart pacing effectiveness of every individual electrode inserted into the target heart zone using a predetermined acceptance criteria, selecting acceptable electrodes for further use as active electrodes, abandoning and optionally removing (at least in some embodiments) rejected pacing electrodes from the heart tissue, optimizing pacing parameters such as intrinsic delays/phase shifts for all accepted pacing electrodes, and adjusting the lead length, position and slack before connection to multiplexer of a pacemaker.

Example

The proof of concept was achieved in the animal experiment using an open chest porcine model. The prototype of a single conduit terminating with a plurality of individual electrodes was created using 6 Fr pacemaker electrode with an extendable-retractable helix spring/screw tip and 4 additional individual electrodes centered around the distal end of the conduit and electrically insulated from each other. The prototype was implanted in 4 adult animals on a beating heart through a small incision in the right atrium and then secured by a purse-string suture to minimize blood loss. The prototype single conduit was manipulated inside the heart, guided manually and assisted by straight and shaped stylets positioned in the inner lumen. Placement was further assisted by intracardiac electrogram recording. The prototype was placed into the area of the triangle of Koch and successfully secured to the endocardium via an extendable spring/screw at the tip thereof. Electrograms were recorded from all recording configurations. The presence of a ventricular electrogram was confirmed in all configurations, the presence of a bundle of His electrogram was confirmed in some configurations, and the presence of an atrial and His electrogram was also seen in some but not all of the recording configurations.

Subsequent testing demonstrated selective and nonselective His bundle capture when pacing between one of the two individual electrodes (used as a negative electrode) and the distal tip of the conduit (used as a positive electrode). Atrial capture was demonstrated between one of the four individual electrodes and the distal tip of the conduit. Furthermore, atrial capture at low output (1 V) with His bundle capture at higher output (6 V) was seen between one individual electrode and the distal tip.

Additional pacing configurations in between the individual electrodes and between the individual electrodes and the ring electrode demonstrated an ability to capture different areas of the heart and variable capture thresholds. In further experiments, in addition to these observations both selective and nonselective His bundle capture was observed when pacing from different individual electrodes.

Examples of a bundle of His signal recording and pacing with different chambers/tissues being captured from the same prototype electrode location are shown in FIGS. 10, 11, 12 and 13. After the animal sacrifice the prototype electrode fixation was confirmed by visual inspection and manual tug. The extendable-retractable spring/screw was shown to be implanted in the triangle of Koch, which effectively positioned the individual electrodes around it in an area of approximately 1 cm in diameter.

Figure 10:
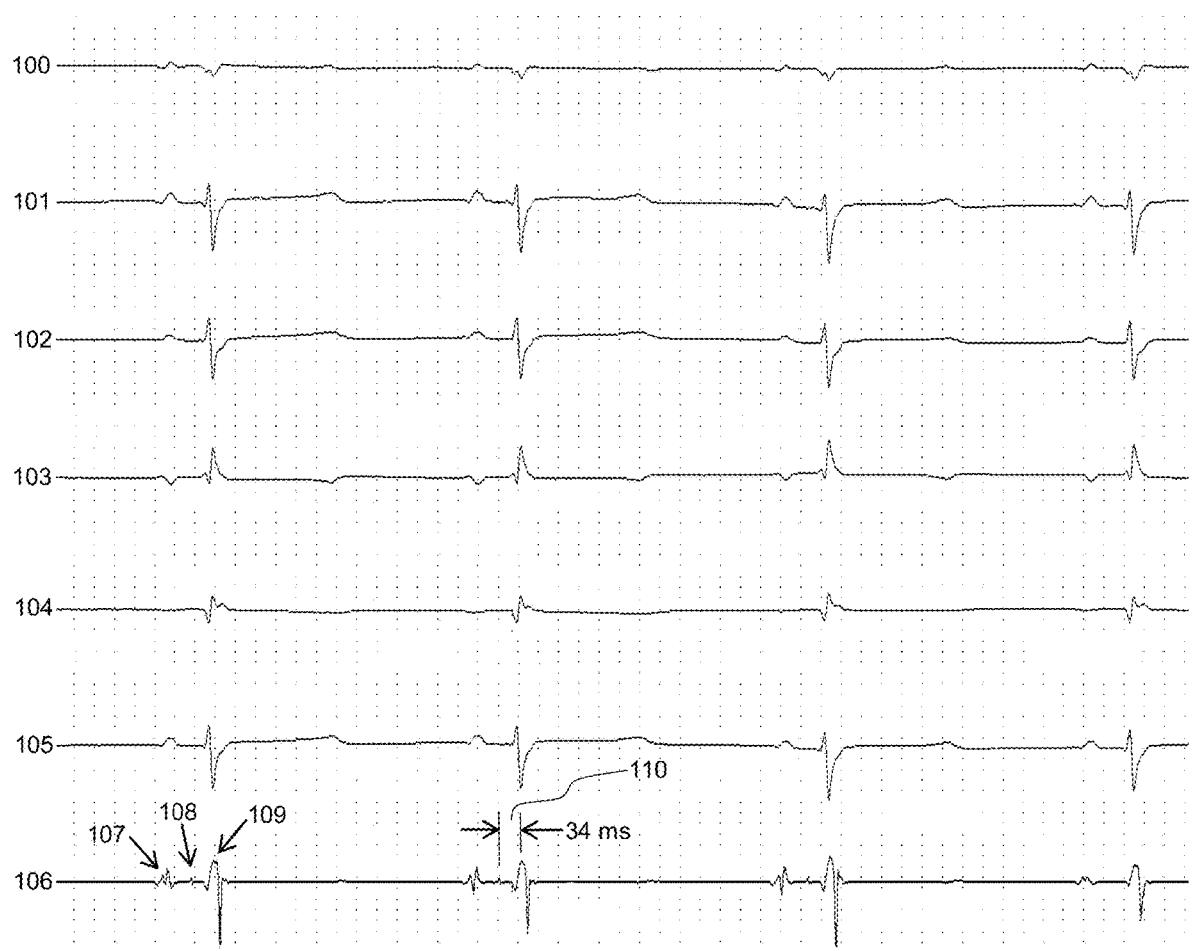
FIG. 10 illustrates measurement of HV interval with intracardiac electrogram recording.

FIG. 10 illustrates exemplary measurement of an HV interval in an animal heart. Generally, the HV interval defines the conduction time from the bundle of His to the first identifiable onset of ventricular activation. The HV interval may be measured at 34 ms, as seen in measurement 110 on the second QRS complex. Shown on tracings 100, 101, 102, 103, 104 and 105 are some of the recorded ECG leads signals, line 106 reflects intracardiac recording from an electrode that is positioned near the bundle of His. Individual positions 107 (atrial electrogram), 108 (His bundle electrogram) and 109 (ventricular electrogram) are shown with arrows.

Figure 11:
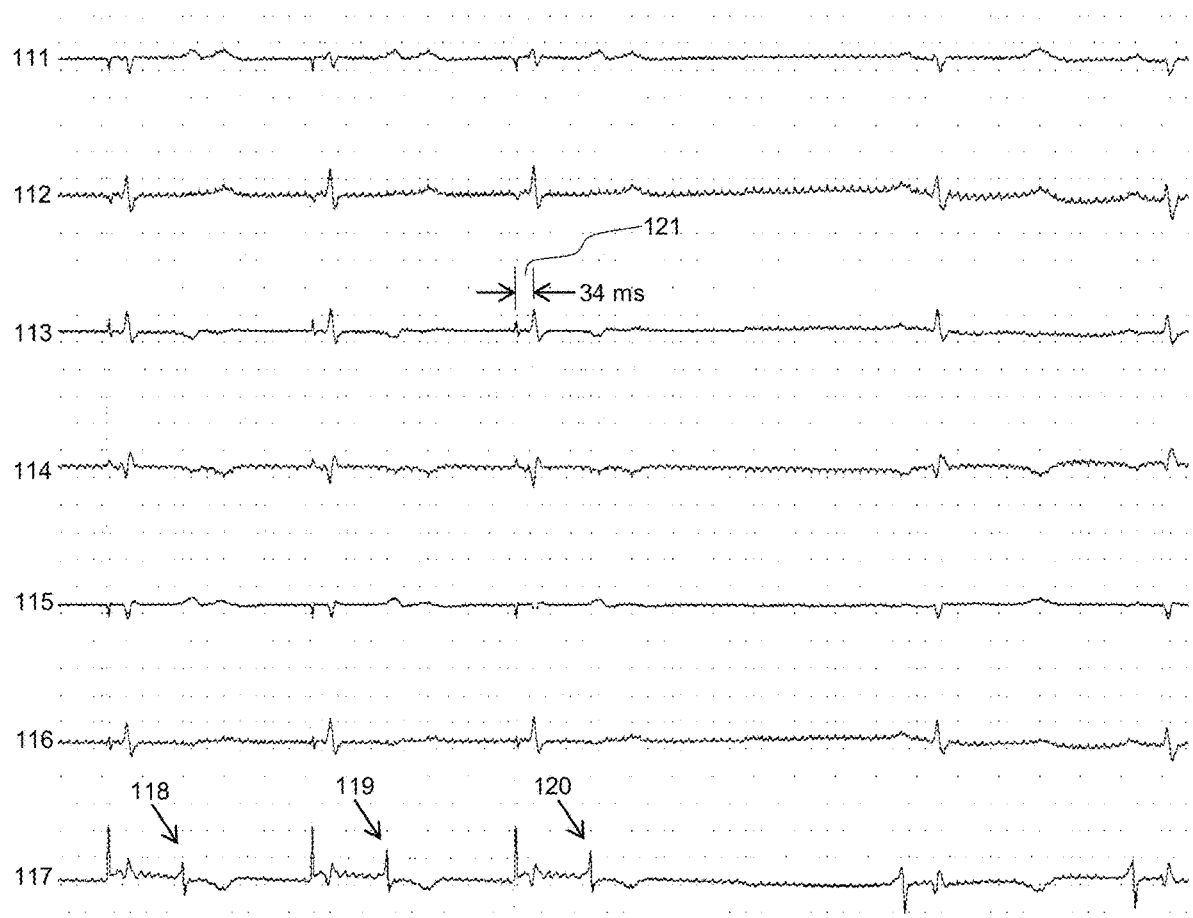
FIG. 11 illustrates selective stimulation of the His bundle with the prototype electrode in an animal heart.

FIG. 11 illustrates selective exemplary stimulation of the bundle of His using individual electrodes like those shown in FIG. 5 in an animal heart. Stimulation between the individual electrodes B3-B4 was attempted. Tracing illustrates selective His bundle capture when pacing in this configuration. After stimulation was discontinued on A1 electrode, the sinus rhythm tracing shows serial activation of the atria (corresponding to a P wave on the ECG tracing) followed by ventricles (corresponding to a QRS complex on the ECG tracing). Shown as tracings 111, 112, 113, 114, 115, and 116 are some exemplary recordings of the ECG leads signals, tracing 117 reflects intracardiac recording between the electrodes B3-B4 that have been implanted into the triangle of Koch. Stimulus to QRS time 121 identical to the HV interval of 34 ms (see 110 in FIG. 10) and narrow QRS may be used to confirm successful selective His bundle capture using the individual electrodes as described above. Retrograde conduction to the atria is seen after the complexes with His bundle capture—as indicated by arrows 118, 119 and 120. This excludes direct capture of the atria by the pacing stimulus.

Figure 12:
FIG. 12 illustrates stimulation of ventricular myocardium by both selective and nonselective His bundle capture with the prototype electrode in an animal heart.

FIG. 12 illustrates activation of the ventricular myocardium by both selective and nonselective His bundle capture in the animal heart. Stimulation was conducted between the individual electrodes B2-B4. Tracings 122, 123, 124, 125, 126 and 127 are some of the ECG lead signals, while tracing 128 reflects intracardiac recording from the prototype electrode that has been implanted into the triangle of Koch (between individual electrodes B2 and B4). Both selective (first 3 QRS complexes) and nonselective His bundle capture (last 3 QRS complexes) are seen as the pacing output is decreased from 7 V to 5 V. Nonselective His bundle capture reflects some capture of the adjacent ventricular myocardium as indicated by slight slurring of the initial QRS complex shown by arrow 129. Stimulus to QRS time during the selective His capture is equal to HV interval shown in FIG. 10—confirming His bundle capture. Retrograde conduction to the atria is seen in tracing 128 as indicated by arrow 130 (same as in FIG. 11). This excludes direct capture of the atria by the pacing stimulus.

Figure 13:
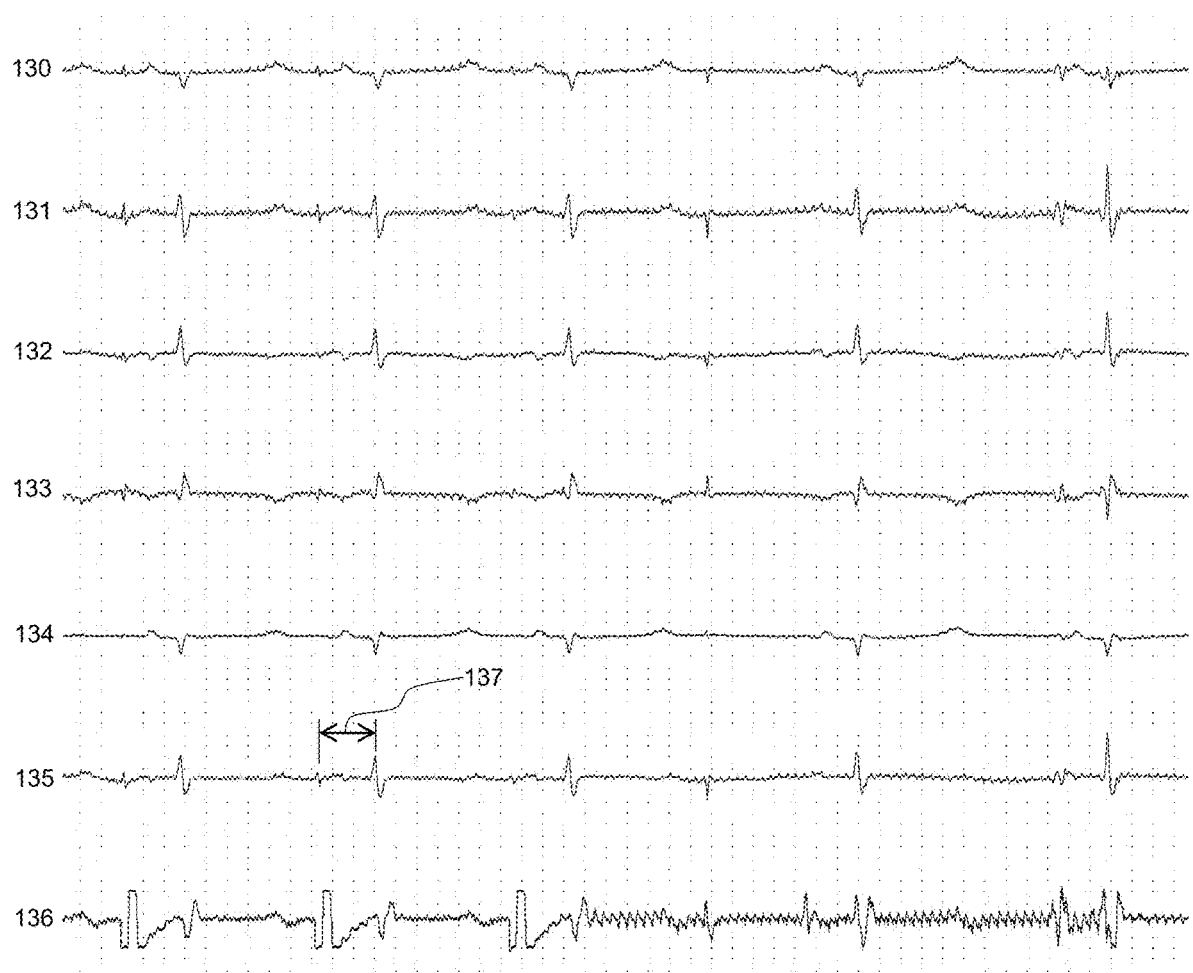
FIG. 13 illustrates stimulation of atrial myocardium by the prototype electrode implanted into the triangle of Koch of an animal heart from the same position where the His bundle capture was obtained from different electrode pairs of the prototype.

Finally, FIG. 13 illustrates pacing of the atria by the prototype electrode implanted into the triangle of Koch of an animal heart. Prototype electrode is still fixed in the same position. Pacing is attempted between the individual electrodes B1 and B2. Atrial capture is seen in the first 2 complexes as indicated by a much longer stimulus-to-QRS time—137. Atrial capture by the pacing stimulus is further confirmed by the appearance of captured P waves in the first 2 complexes on tracings 130, 131, 132, 133, 134 and 135. First 2 PQRS complexes are paced, whereas the last 3 PQRS complexes are not and show native conduction. Shown on tracings 130, 131, 132, 133, 134 and 135 are the ECG leads signals, whereas tracing 136 reflects intracardiac recording between the individual electrodes B1-B2 from the prototype that has been implanted into the triangle of Koch in the same position where His bundle capture was demonstrated from other electrode pairs (FIGS. 11-12).

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of providing cardiac pacing comprising the steps of:
   a. providing a flexible single conduit housing a plurality of individual wires extending therethrough and positioned alongside each other at least in a portion of said single conduit, said plurality of individual wires terminating with a plurality of corresponding individual electrodes located at a distal end of said single conduit,
   b. advancing said single conduit to position said distal end thereof near a cardiac tissue target area while said plurality of individual electrodes are held in a collapsed position next to a center of said distal end of said single conduit,
   c. expanding said plurality of individual electrodes to an expanded position forming an expanded scattered pattern of said plurality of individual electrodes about and away from said center of said distal end of said single conduit,
   d. implanting said individual electrodes into said cardiac tissue target area while in said expanded scattered pattern,
   e. interrogating each individual electrode of said plurality of individual electrodes to determine a subset of said plurality of individual electrodes meeting a predetermined acceptance criteria for capturing of and pacing the heart, and
   f. initiating cardiac capture and pacing using at least some of individual electrodes of said subset of individual electrodes meeting said predetermined acceptance criteria, said at least some individual electrode connected via corresponding individual wires of said single conduit to a pacemaker located outside the heart.

2. The method as in claim 1, wherein said cardiac tissue target area comprises triangle of Koch, bundle of His and surrounding areas.

3. The method as in claim 1, wherein said predetermined acceptance criteria in step (e) is appearance of an acceptable paced P-wave on an ECG tracing when said cardiac pacing is desired to correct an atrial arrhythmia.

4. The method as in claim 1, wherein said predetermined acceptance criteria in step (e) is selective capture of the bundle of His and/or triangle of Koch.

5. The method as in claim 1, wherein said predetermined acceptance criteria in step (e) is nonselective capture of the bundle of His and/or triangle of Koch.

6. The method as in claim 1, wherein said predetermined acceptance criteria in step (e) is appearance of an acceptable QRS complex on an ECG tracing when said cardiac pacing is desired to correct atrio-ventricular, atrial, or ventricular conduction disturbances.

7. The method as in claim 1, wherein in step (e) said subset of individual electrodes is further stratified based on a lowest voltage of achieving said predetermined acceptance criteria.

8. The method as in claim 1, wherein in step (f) remaining individual electrodes of said subset of individual electrodes are left in a passive state implanted in said cardiac tissue.

9. The method as in claim 8, wherein said step (f) further including a step of re-activation of said remaining individual electrodes when a malfunction of the previously selected electrodes is detected.

* * * * *